United States Patent [19]
Johnson

[11] Patent Number: 5,449,384
[45] Date of Patent: Sep. 12, 1995

[54] DYNAMIC ANNULUS HEART VALVE EMPLOYING PRESERVED PORCINE VALVE LEAFLETS

[75] Inventor: Keith M. Johnson, Coon Rapids, Minn.

[73] Assignee: Medtronic, Inc., Minneapolis, Minn.

[21] Appl. No.: 952,111

[22] Filed: Sep. 28, 1992

[51] Int. Cl.6 .................................................. A61F 2/24
[52] U.S. Cl. ........................................................ 623/2
[58] Field of Search ............................. 623/2, 900, 901

[56] References Cited

U.S. PATENT DOCUMENTS

| | | | |
|---|---|---|---|
| 4,247,292 | 1/1981 | Angell | 623/2 |
| 4,339,831 | 7/1982 | Johnson | 623/2 |
| 4,451,936 | 6/1984 | Carpentier et al. | 623/2 |
| 4,692,164 | 9/1987 | Dzemeshkevich et al. | 623/900 X |
| 5,156,621 | 10/1992 | Navia et al. | 623/2 |

Primary Examiner—David Isabella
Attorney, Agent, or Firm—Reed A. Duthler; Harold R. Patton

[57] ABSTRACT

A prosthetic heart valve having a frame comprising a plurality of struts joined together at a common point and extending radially from the common point to free ends spaced from one another and a plurality of preserved tissue valve leaflets, each having a free edge, mounted to said frame means such that said free edges of said leaflets extend between the free ends of said frame struts. Each of the leaflets are provided with an associated strip of aortic tissue and the strips of aortic tissue are joined to one another to enclose the frame struts so that no synthetic materials are exposed to the bloodstream with the exception of suture material used to join the adjacent strips of aortic tissue.

8 Claims, 5 Drawing Sheets

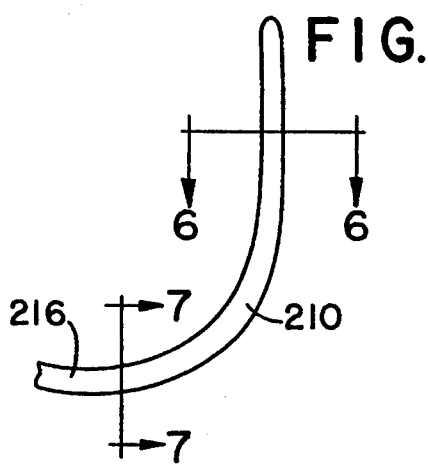
FIG. 5
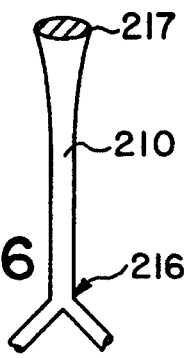
FIG. 6
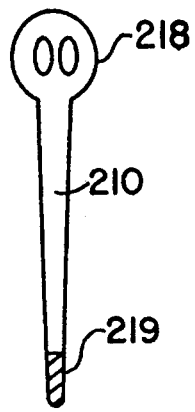
FIG. 7
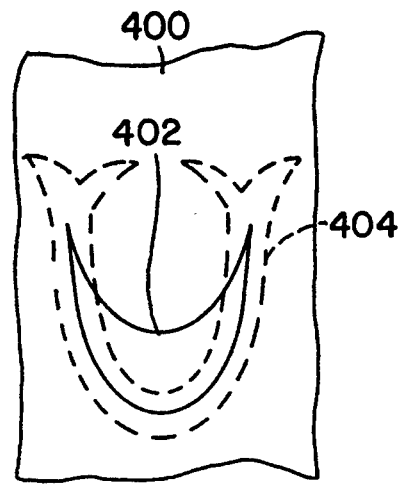
FIG. 8
FIG. 9
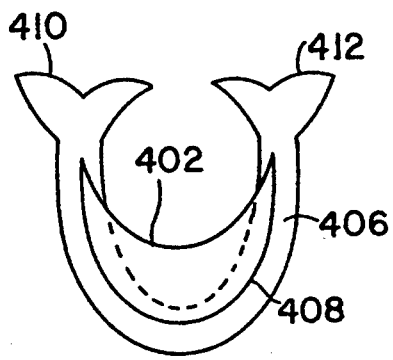
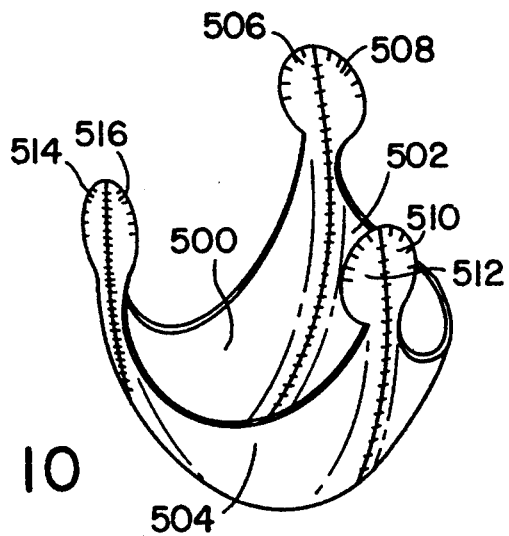
FIG. 10

DYNAMIC ANNULUS HEART VALVE EMPLOYING PRESERVED PORCINE VALVE LEAFLETS

BACKGROUND OF THE INVENTION

The present invention relates to prosthetic heart valves generally, and more particularly to heart valves employing preserved animal tissue or flexible polymers as leaflets.

Prosthetic heart valves have been used for more than 30 years for replacement of diseased natural heart valves. The use of preserved porcine heart valves alone, or in association with a reinforcing stent or frame has been widely practiced. Valves constructed using preserved pericardial or dura mater tissue, mounted to stents or frames have also been employed. It has also been repeatedly proposed to employ flexible synthetic materials as substitutes for preserved tissue in valves of this type.

One proposal for constructing a synthetic heart valve employing flexible polymer valve leaflets is set forth in U.S. Pat. No. 4,339,831 issued to Johnson. The disclosed valve employs a framework of three curved flexible struts each joined at one end to a common central point and extending therefrom in the same direction, at equal angles from each other with the free ends of the struts located spaced equidistantly from one another. The free ends are each provided with sewing pads for attachment of each free end separately to the natural tissue annulus by means of sutures. The valve is provided with a hemispherically shaped membrane adapted to fit over and be attached to the framework so that three partial hemispheric segments or leaflets are defined. Each leaflet extends between adjacent frame struts in such a manner that the free edge of each leaflet can contact the tissue annulus when the valve is closed and can move inward, away from the tissue annulus when the valve is open.

BRIEF SUMMARY OF THE INVENTION

The present invention is an improved heart valve which is structurally similar to that disclosed in the above-cited patent issued to Johnson. However, the inventor has now determined that a valve having the mechanical benefits as the disclosed valve, without the difficulties attendant to construction of a valve employing synthetic leaflet materials, can be accomplished by excising individual porcine heart valve leaflets and aortic tissue and mounting them to a frame generally as indicated in the above-cited Johnson patent, but reversed from their normal configuration. This improvement in and of itself overcomes any problems associated with the use of synthetic materials, which have not proved to be of the durability or the valuable low thrombogenicity of preserved porcine leaflets.

In addition, the valve leaflets are coupled to the frame in such a fashion that the frame is completely enclosed by the natural tissue, and such that only valve leaflet or aortic wall tissue is exposed to the blood, rather than plastic, metal or cloth coverings typically found in prosthetic heart valves. The only synthetic materials exposed to the flow of blood are small areas of suture material used to attach the valve leaflets to one another. In conjunction with this aspect of the invention, the valve framework has also been modified such that rather than employing fabric covered pledgets to attach the free ends of the struts to the aortic tissue of the patient, expanded surface area portions of the frame are provided, covered with preserved porcine tissue. Optionally or in addition, sutures through the free ends of the struts may pass through the aortic wall and engage fabric covered pledgets located on the exterior of the aortic wall.

In addition to the above improvements to the structure of the valve, the inventor has also developed an improved method of mounting the valve to the patient's tissue, in aortic valve replacements. Rather than mounting the free ends of the valve struts to the aortic annulus, as disclosed in the above-cited Johnson patent, the inventor has determined that it is beneficial to locate the valve such that the free ends of the struts are attached to the fibrous sino-tubular ridge, located above the sinuses of the Valsalva, at the base of the aorta. Each free end of a valve strut is preferably located intermediate to adjacent ones of the sinuses of Valsalva. Because the valve leaflets now hang down into the sinuses of Valsalva, the increased diameter of the aorta in the region of the sinuses now surrounds the valve structure. As a result, the net cross sectional area for blood flow through the valve is increased as compared to a similar valve mounted at the aortic annulus.

BRIEF DESCRIPTION OF THE DRAWINGS

FIGS. 5, 6 and 7 illustrate the structure of an individual valve strut of the framework illustrated in FIG. 3.

FIG. 8 illustrates a valve leaflet attached to aortic wall tissue, and illustrates the cutting pattern employed to remove the valve from the adjacent tissue.

FIG. 9 illustrates an excised valve leaflet and associated aortic wall tissue.

FIG. 10 is a prospective view of an assembled heart valve according to the present invention.

DETAILED DESCRIPTION OF THE PREFERRED EMBODIMENT

Figure 1:
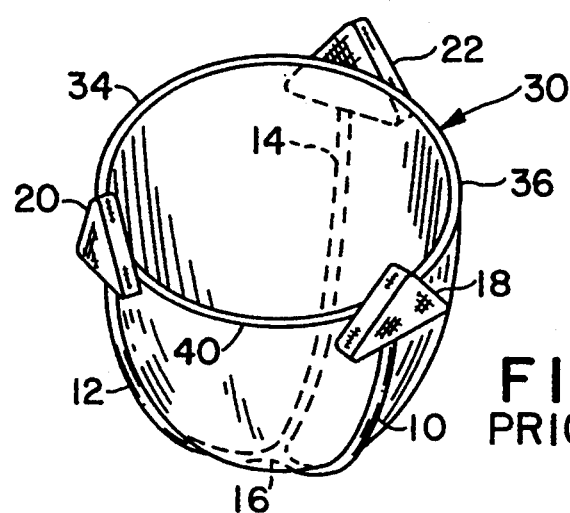
FIG. 1 is a drawing of the prior art heart valve disclosed in the above-cited Johnson patent.

FIG. 1 illustrates the valve disclosed in the above-cited Johnson patent. The valve includes a framework comprising three arcuate struts 10, 12 and 14 joined together at a point 16. The struts forming the framework are made of a resilient or springy material such as polytetraflouroethylene. At the end of each strut is a suture pad or pledget 18, 20, 22. The suture pads may be formed of open mesh dacron polymer cloth sewn in layers or of several layers of thin sheets of expanded polytetraflouroethylene aligned at 90° to one another and bonded together along the pad framework. The valve leaflet is formed of a flexible membrane 30 which is formed of several layers of expanded polytetraflouroethylene formed into a hemispheric or parabaloid shape to fit within the shape of the framework. The membrane is attached to struts 10, 12 and 14 at all points extending from the common point of joinder 16 to the suture pads 18, 20 and 22. The flexible membrane 30 upon attachment to the framework thus possesses three hemispheric or paraboloid leaflets or segments having free edges 34, 36 and 40.

The valve as illustrated may be mounted for use as either aortic or mitral valve, with the suture pads 18, 20, 22 sutured directly to the mitral or aortic valve annulus with the struts extending from the suture pads in an upstream direction. In response to pressure on the upstream side, the leaflets fold inwardly together, along fold lines defined by the struts. In response to back pressure from the downstream direction, the leaflets balloon outward and into contact with the aortic or mitral annulus, sealing the annulus.

The overall functioning and configuration of the valve of the present invention is similar to that illustrated in FIG. 1. However, substantial improvements and modifications have been made by the inventor, which are believed to provide the opportunity for enhanced performance, durability and biocompatibility.

Figure 2:
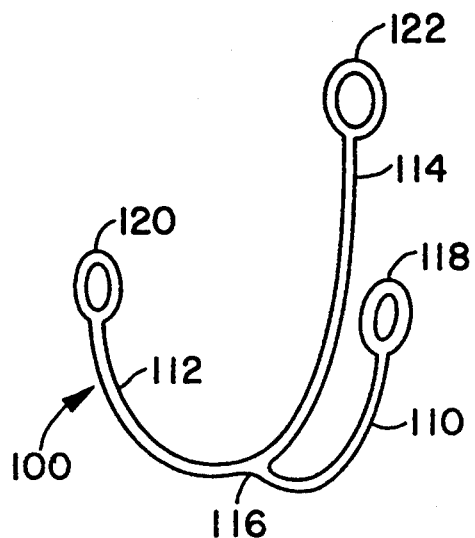
FIGS. 2, 3 and 4 are alternative valve framework designs.
Figure 3:
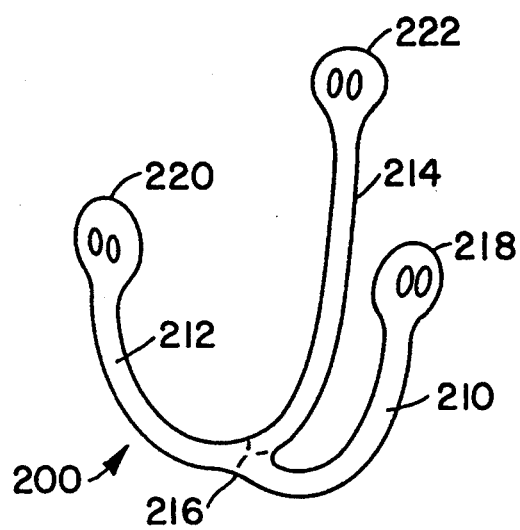
Figure 4:
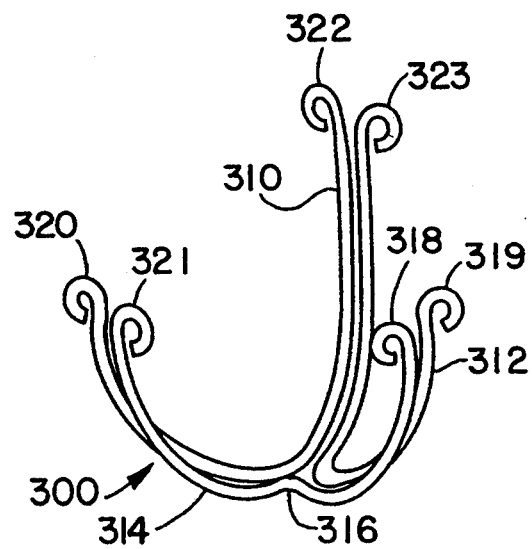

FIGS. 2, 3 and 4 illustrate alternative frameworks which may be employed in conjunction with a valve according to the present invention. Like the framework of FIG. 1, all three of these improved frameworks provide for radial flexibility to allow the frameworks to conform to the patient's natural tissue configuration.

FIG. 2 illustrates a framework formed out of a biocompatible metal wire, for example, ELGILOY wire, comprising three arcuate struts, 110, 112 and 114 joined together at a common point 116. At point 116, each strut defining an angle of approximately 120° with respect to the next strut, at point 116. The free end of each strut is provided with a loop 118, 120, 112. Generally, the configuration of the framework is the same as the framework illustrated in FIG. 1. However, rather than employing fabric covered suture pads coupled to the ends of the struts, the rings 118, 122 and 120 are covered with porcine tissue, to define suture pads, which are sutured to the patient's tissue. FIG. 3 illustrates a plastic framework 200, preferably fabricated of a relatively rigid biocompatible plastic, such as DELRIN. This framework is also similar in overall configuration to the framework illustrated in FIGS. 1 and 2. The framework comprises three arcuate struts 210, 212 and 214 joined together at a common point 216. The free end of each strut is provided with a flattened pad 218, 220, 222 each of which is provided with two apertures through which sutures may be passed for securing the framework to the patient's tissue.

FIG. 4 shows an alternative valve framework 300, fabricated of three separate metal wires 310, 312 and 314, preferably fabricated of a biocompatible metal such as Elgiloy. The three wires are each bent into two arcuate segments, angled at 120° from each other. The three wires are assembled as illustrated, such that the three wires together define three struts having the same overall configuration as the struts illustrated in FIGS. 1, 2 and 3, with each strut formed of the free end of two adjacent wires. Each end of each wire is provided with a loop 320, 321, 322, 323, 318 and 319 through which sutures may be passed to secure the framework to body tissue. The wires may simply be arranged adjacent one another and may be held together by the tissue as installed on the framework or, alternatively, may be lashed together by means of sutures or other appropriate material, prior to mounting of valve tissue to the framework.

The flexible strut designs in FIGS. 2, 3 and four all provide for deflection of the free ends of the struts. When the valve is installed in the aorta as described below, this feature allows the free ends of the stut to follow the expansion of the aorta during blood flow through the valve.

FIGS. 5, 6, and 7 illustrate the configuration of a single strut 210 of the framework illustrated in FIG. 3. FIG. 5 illustrates the views along which sectional views 6 and 7 are taken. As can be seen in FIGS. 6 and 7, the framework is formed such that the struts display a non-uniform cross-section, which varies along the length of the strut. Taking the point of junction 216 as the center of the framework, and taking a line through point 216 and perpendicular to the struts as the axis of the structure, the free ends of the struts display a reduced thickness in a radial direction as illustrated at 217. Near the point of juncture 216, the struts are substantially thicker axially and radially than circumferentially at 219. This transition in cross-section provides a structure which is highly resistent to stress applied along the axis of the framework, in those areas adjacent the point of juncture 216, but which retains radial flexibility adjacent the free ends of the struts to allow them to move with and conform to the tissue which they are attached when the valve is implanted.

FIG. 8 shows a piece of porcine aortic tissue 400 with the left coronary leaflet 402 attached. For purposes of this illustration, the adjacent leaflets are presumed to have already been excised. the left coronary leaflet is chosen as it extends for approximately 120 degrees around the circumference of the porcine valve.

Illustrated by dotted line 404 is the outline along which the aortic tissue 400 is trimmed in order to provide a single leaflet for use in conjunction with the valve of the present invention. In conjunction with trimming away the unwanted aortic tissue, the retained tissue may optionally also be shaved to reduce its thickness. For purposes of sizing the leaflet to the framework, a leaflet from a porcine valve having approximately the same circumference as the framework is selected.

FIG. 9 illustrates the trimmed and removed valve leaflet and associated aortic tissue. As illustrated, the leaflet is removed, along with a strip of aortic wall material 406, running around the periphery 408 of the valve leaflet 402. Also excised are tabs 410 and 412, which are employed to enclose the loops or pads located on the free ends of the valve framework, to provide suture pads.

FIG. 10 illustrates a view of the valve as assembled. As illustrated, three valve leaflets 500, 502 and 504 are mounted to the framework such that the aortic wall tissue associated with the edge of each leaflet is wrapped around the struts, and sewn to the aortic wall tissue of the adjacent leaflet. The tabs 506, 508, 510, 512, 514 and 516 are similarly folded over the loops or pads at the ends of the struts and sewn together at their adjoining free edges to completely enclose the loops or pads formed on the free ends of the struts. The resulting structure is a valve which is entirely covered with porcine heart tissue, and has no exposed synthetic materials other than very limited area of exposed suture material.

Figure 11:
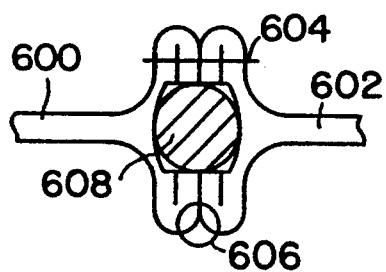
FIGS. 11–15 illustrate alternative methods of attaching the valve leaflet tissue to the frameworks illustrated in FIGS. 2, 3 and 4.
Figure 12:
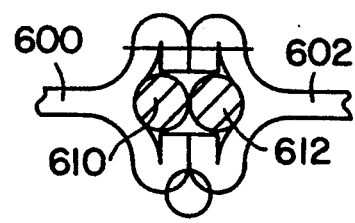

FIGS. 11-15 illustrate alternate ways of joining adjacent leaflets and mounting them to the framework. FIG. 11 is a cross-sectional view through a strut 608, which may be part of a framework as illustrated in FIG. 2 or FIG. 3. The leaflets 600 and 602 are each provided with a strip of attached aortic wall, the cut edges of which are folded over adjacent one another and sutured together by means of sutures as illustrated diagrammatically at 604 or 606, such that the cut edges of the strips of aortic tissue are completely enclosed. Enclosing the cut edges of the aortic tissue is believed to be beneficial in reducing the frequency of formation of hematomas. FIG. 12 illustrates leaflets 602 and 600, mounted in the same fashion around two wires 610, 612 of a three wire frame as illustrated in FIG. 4.

Figure 13:
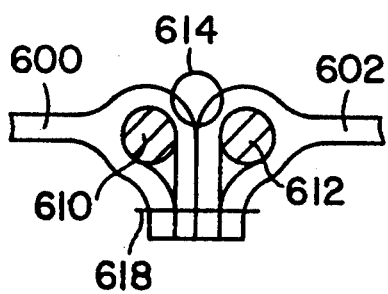

FIG. 13 discloses an alterative mechanism for mounting the leaflets 600, 602 around the same two wires 610 and 612 of as in FIG. 12. In this case, the associated strip of aortic wall tissue attached to each of leaflets 600 and 602 is first wrapped around an individual one of the wires 610, 612, with the resulting structure then sutured together by means of sutures as illustrated diagrammatically at 614 and 618.

Figure 14:
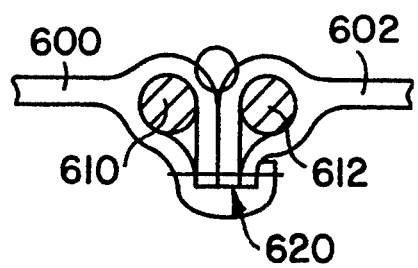

FIG. 14 illustrates yet another alternative method for attaching leaflets 600 and 602 to two wires 610 and 612 of a three wire frame as illustrated in FIG. 4. In this case, a wider band of aortic wall material 620 is retained along one edge of each of the leaflets, allowing the wall to be wrapped around the other edges of the aortic wall material, and sutured thereto, thereby avoiding any exposed free edges of the aortic wall material.

Figure 15:
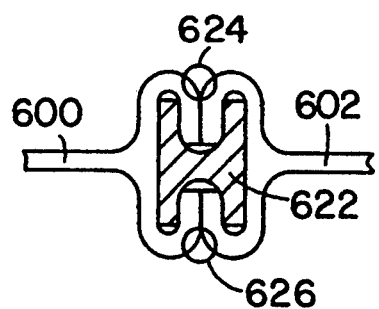

FIG. 15 illustrates the attachment of leaflets 600 and 602 to the strut 622 of an additional alternative frame design having an H-shaped cross-section. The frame may be constructed of biocompatible plastic, similar to the framework illustrated in FIG. 3, but provided with grooves on its inner and outer surfaces. In this case, the free edges of the aortic wall material are tucked into grooves in the frame 622 and are coupled to one another and to the frame by means of sutures illustrated diagrammatically at 624 and 626.

Figure 16:
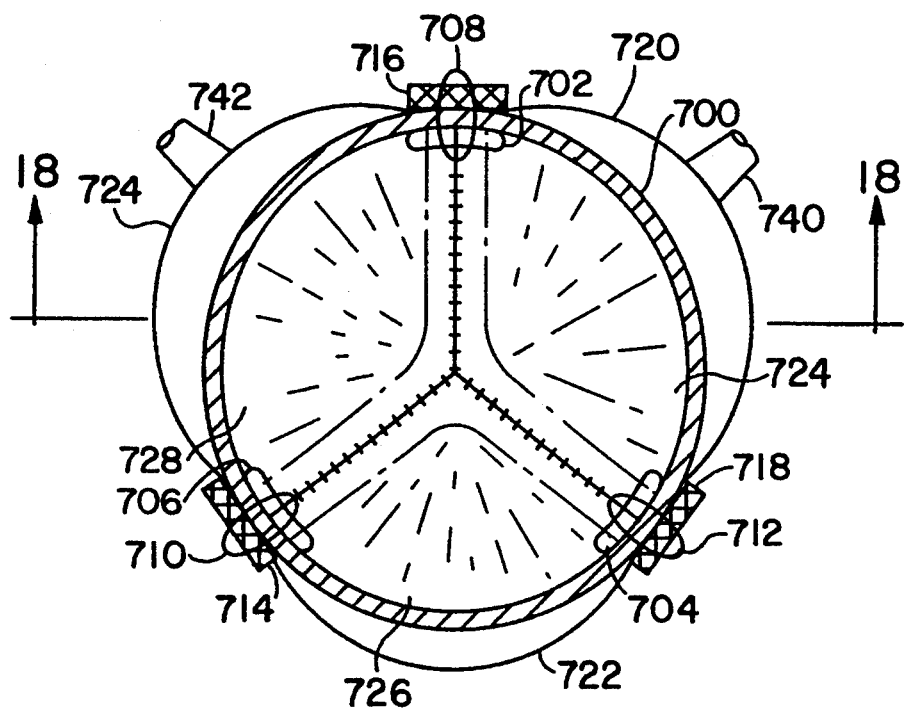
FIG. 16 is a cross-sectional view through the aorta, looking toward the heart, illustrating an installed valve in the closed position.

FIG. 16 illustrates a valve according to the present invention as implanted. The view is taken looking down the aorta toward the heart. The wall of the aorta in the vicinity of the sino-tubular ridge is illustrated in cross-section at 700. This ridge serves as the mounting point for the valve. As discussed above, each strut end is provided with a suture pad, 700, 702, 704, 706, covered with porcine tissue, through which sutures may be passed. Sutures 708, 710 and 712 are illustrated diagrammatically, shown passing through pads 702, 704, 706 and the aortic wall 700. Pledgets or suturing pads 714, 716 and 718 are optionally provided mounted to the exterior wall of the aorta.

As illustrated, between the sino-tubular ridge 700 and the heart are located the three sinuses of Valsalva 720, 722 and 724. These sinuses define three outwardly extending bulges in the aortic wall, located between the sino-tubular ridge and the aortic annulus. Illustrated in the closed position, the three leaflets, 724, 726 and 728 are shown with their outer surfaces in contact with the tissue annulus below the coronary ostia of the left coronary artery 742 and the right coronary artery 740, in order to seal the valve in the closed position. In order that the present invention function optimally, it is believed desirable that the porcine leaflets be preserved using a low pressure fixation technique, allowing retention of substantial radial elasticity of the leaflets, so that they may stretch and expand in order to conform to the tissue annulus.

Figure 17:
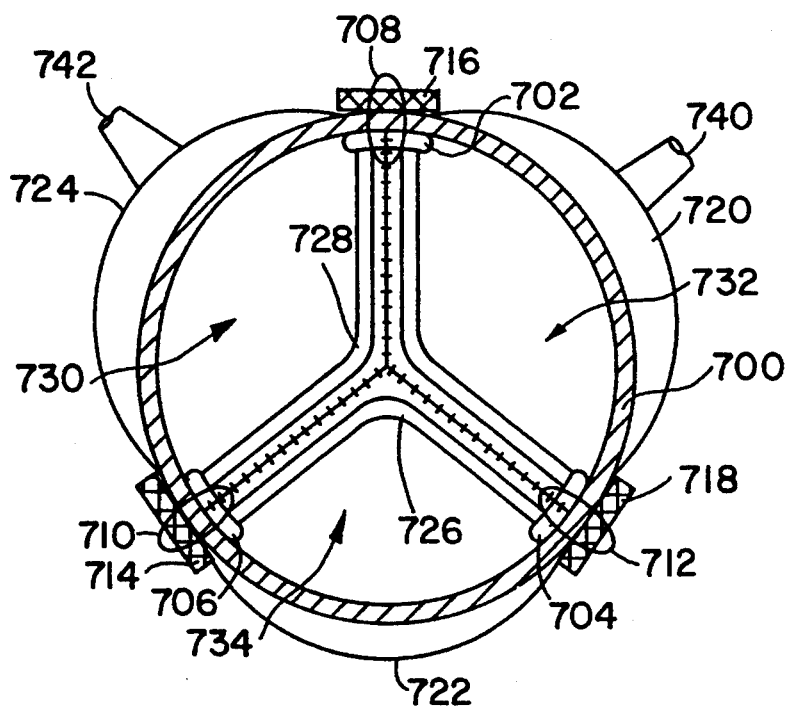
FIG. 17 is a cross-sectional view through the aorta, looking toward the heart, illustrating a valve according to the present invention in the open position.

FIG. 17 illustrates the same valve, in an open position wherein the leaflets 724, 726 and 728 are folded adjacent to one another along fold lines defined by the framework struts, defining three flow passages 730, 732 and 734. In the open position, the lower portions of the leaflets, which pass through the aortic annulus will fold tightly against one another. However, the upper edges of the leaflets, as illustrated do not collapse completely adjacent one another, due to expansion of the aorta and corresponding movement of the valve struts during blood flow through the valve. The upper edges of the valve leaflets are located upstream of the suture pads and are thus located intermediate the sinuses of Valsalva. As such, the cross sectional area of the three flow passages, as measured between the upper edges of valve leaflets and the adjacent sinuses, still provides a total area for blood flow at least equal to that of the aortic annulus.

Figure 18:
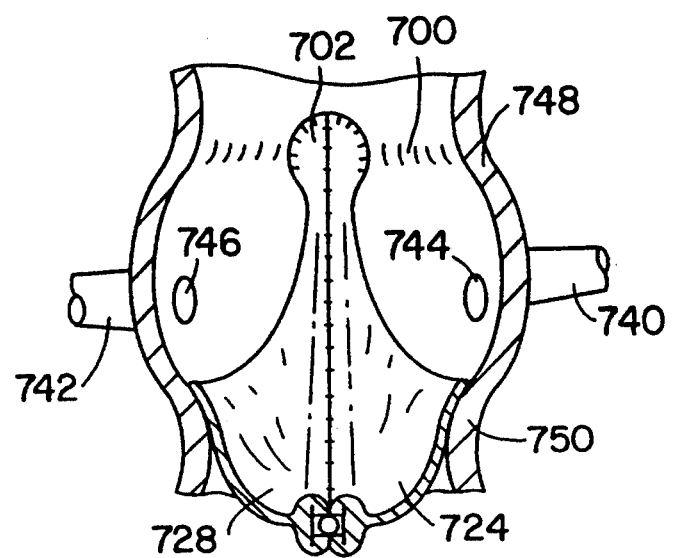
FIG. 18 is a sectional view through the valve as mounted in the aorta.

FIG. 18 shows a sectional view through the valve as mounted to the aorta 748, with the valve leaflets 728, 724 in the closed position. In this view it can be seen that the suture pad 702 is mounted to the sino-tubular ridge 700 and that the outer surfaces of leaflets 724, 728 are form a seal against the aortic annulus 750. The valve thus provides a seal upstream from the ostia 744, 746 of the right and left coronary arteries 740, 742, respectively.

While the disclosed embodiments are described in the context of their use as aortic valves, it should be understood that valves according to the present invention may also usefully be employed as pulmonary, mitral or tricuspid valves. It is believed that the invention as disclosed in the embodiments illustrated above could be employed as a pulmonary valve and would be especially valuable in this context. For use as a mitral or tricuspid valve, the disclosed embodiments would be modified by placing the suture pads on the struts intermediate their point of joinder and their free ends, so that as installed, the pads are located along the tissue annulus remaining after removal of the patient's valve.

While specific materials have been suggested for use in constructing the frames of the valves, other plastics and metals are also believed to be suitable. Similarly, while the valve is disclosed as employing porcine valve leaflets, preserved valve leaflets from human or other sources may also be employed within the scope of the invention. The embodiments disclosed above are therefore intended merely to be examples of the present invention and should not be construed as limiting with regard to the scope of the claims which follow. In conjunction with the above disclose, I claim:

1. A prosthetic heart valve, comprising:
    a flexible frame means comprising a plurality of arcuate frame struts joined together at a common point and extending radially from said common point to free ends spaced from one another; and
    a plurality of preserved natural heart valve leaflets, each having a first free edge, mounted to said frame means such that said free edges of said leaflets extend between the said free ends of said frame struts wherein said leaflets are each provided with a second edge, having an associated strip of aortic tissue and wherein said strips of aortic tissue are joined to one another to enclose said frame struts.

2. A valve according to claim 1 wherein each of said frame struts is provided with suturing means for allowing passage of sutures therethrough and wherein said strips of aortic tissue are joined to one another to cover said suturing means.

3. A valve according to claim 1 further comprising sutures, joining said strips of aortic tissue to one another.

4. A valve according to claim 1 wherein said strips of aortic tissue have edges and are joined to one another such that no said edges of said aortic tissue are exposed.

5. A prosthetic heart valve, comprising:
 a flexible frame means; and
 a plurality of preserved natural heart valve leaflets each provided with an edge having an associated strip of aortic tissue and wherein said strips of aortic tissue are joined to one another to enclose said frame.

6. A prosthetic heart valve according to claim 5 wherein said strips of aortic tissue completely enclose said frame.

7. A valve according to claim 6 or claim 6 wherein said strips of aortic tissue have edges and are joined to one another such that no said edges of said aortic tissue are exposed.

8. A valve according to claim 5 or claim 6 wherein said frame is provided with suturing means for allowing passage of sutures therethrough and wherein said strips of aortic tissue are joined to one another to cover said suturing means.

* * * * *